United States Patent
Rodolfi et al.

(10) Patent No.: US 10,683,470 B2
(45) Date of Patent: Jun. 16, 2020

(54) PRODUCT FOR CLEANING, SANITIZING AND HYGIENIZATION

(71) Applicant: COPMA S.C.A.R.L., Ferrara (IT)

(72) Inventors: Alberto Rodolfi, Cento (IT); Elisabetta Caselli, Ferrara (IT)

(73) Assignee: COPMA S.C.A.R.L., Ferrara (IT)

( * ) Notice: Subject to any disclaimer, the term of this patent is extended or adjusted under 35 U.S.C. 154(b) by 9 days.

(21) Appl. No.: 15/567,869

(22) PCT Filed: Apr. 20, 2016

(86) PCT No.: PCT/IB2016/052230
§ 371 (c)(1),
(2) Date: Oct. 19, 2017

(87) PCT Pub. No.: WO2016/170479
PCT Pub. Date: Oct. 27, 2016

(65) Prior Publication Data
US 2018/0134993 A1   May 17, 2018

(30) Foreign Application Priority Data

Apr. 22, 2015 (IT) .................. 102015000012659

(51) Int. Cl.
| | |
|---|---|
| *C11D 3/38* | (2006.01) |
| *C11D 1/38* | (2006.01) |
| *C11D 1/66* | (2006.01) |
| *C11D 1/88* | (2006.01) |
| *C12R 1/11* | (2006.01) |
| *C12R 1/125* | (2006.01) |

(52) U.S. Cl.
CPC .............. *C11D 3/381* (2013.01); *C11D 1/38* (2013.01); *C11D 1/66* (2013.01); *C11D 1/88* (2013.01); *C11D 3/38* (2013.01); *C12R 1/11* (2013.01); *C12R 1/125* (2013.01); *C12N 2795/14111* (2013.01); *C12N 2795/14211* (2013.01); *C12N 2795/18111* (2013.01)

(58) Field of Classification Search
None
See application file for complete search history.

(56) References Cited

U.S. PATENT DOCUMENTS

| | | | | |
|---|---|---|---|---|
| 2004/0175407 A1* | 9/2004 | McDaniel | ................ | A62D 3/02 424/423 |
| 2013/0184196 A1* | 7/2013 | Brooke | .................. | A01N 63/00 510/461 |

FOREIGN PATENT DOCUMENTS

| | | | | |
|---|---|---|---|---|
| EP | 0414304 A2 * | 2/1991 | ............. | A01N 63/00 |
| EP | 0414304 A2 | 2/1991 | | |
| EP | 1967548 A1 | 9/2008 | | |

\* cited by examiner

*Primary Examiner* — Nghi V Nguyen
(74) *Attorney, Agent, or Firm* — R. Neil Sudol; Henry D. Coleman (57) ABSTRACT

Product for cleaning, sanification and hygienization, comprising a base solution with sanificant and/or hygienizing action to which probiotic bacteria and bacteriophage elements are mixed; the probiotic bacteria being preferably of the *Bacillus subtilis*, *Bacillus megaterium* and *Bacillus pumilus* genera, while the bacteriophage elements comprise, as an alternative or in combination, bacteriophages of the Caudavirales, Microviridae, Leviviridae, Inoviridae, Tectiviridae, Corticoviridae families.

4 Claims, 10 Drawing Sheets

PRODUCT FOR CLEANING, SANITIZING AND HYGIENIZATION

FIELD OF THE INVENTION

The present invention relates to the technical field of cleaning, sanitizing and hygienization, in particular of ambients and surfaces.

Currently, to the possibility of controlling and eliminating chemical and/or microbial contamination which can be dangerous for people's health is being given always more importance.

DESCRIPTION OF THE PRIOR ART

The traditional, currently used products and methods for cleaning and sanification are not more satisfying both for the occurrence of multi-resistant microbial species (so called "superbugs") and for avoiding the use of chemical antimicriobial disinfectant substances with high environmental impact.

This is to be related to the incapacity of traditional (chemically formulated) detergents and hygienization means to act against the re-contamination of the surfaces treated.

Such re-contamination is ultimately the main responsible for infections associated to contaminant microorganisms (bacteria and fungi) which can be transmitted by contact with the contaminated surfaces.

Another drawback of traditional detergents/hygienization means relates to the incapacity to control the occurrence of antibiotics multi-resistant bacterial species. On the contrary, the use of determined substances (and the selective pressure exerted on contaminant microorganisms) is at times directly correlated to the selection of resistant microbial species, which is highly undesirable since potentially associated to the development of infections which are more dangerous for people's health since difficult to be eradicated by means of pharmacological therapy.

In the hospital field, it is noted that the infections represent one of the more frequent complications of hospitalization (5%-15% of all the hospitalized patients) since the boundary and furniture surfaces act as receptacle for microorganisms, thus increasing the risk of contamination by direct and/or indirect contact with the patient.

Currently, there are known products for cleaning and of surfaces today used by the Applicant in the use of the system known with the trade name "Probiotic Cleaning Hygien System" (PCHS), in which probiotic bacteria spores, in particular of *Bacillus* genus, are introduced in a mix with detergent, sanificant and hygienizing action.

Such products use a "bio-control" approach based on the fact that the probiotic (not pathogenic) microorganisms can colonize the surfaces to be cleaned and hygienized, thus competing with the proliferation of other species potentially dangerous for people's health.

*Bacillus* genus bacteria represent a great group of sporogenic gram-positive bacteria, ubiquitous in nature and occurring also in the human intestine.

The spores formed by the *Bacillus* bacteria can remain vital for very long periods, thanks to their resistance to drying, heat and many chemical substances, and therefore are ideal for probiotic applications in the sanitizing field.

In addition, it is to highlighted that, from a safety point of view, the pathogenic risk of the *Bacillus* species occurring in the products used in the PCHS application is considered low/null (nonpathogenic).

The Applicant has shown that the products for cleaning and sanitizing of the type used in the application of the PCHS system owe their action on the one hand to the base mix detergent/sanificant/hygienization means, which according to EC regulations contains nonionic surfactants (5-15%), cationic surfactants (<5%), amphoteric surfactants (<5%) in environmentally sustainable concentrations and is responsible for the immediate cleaning action.

On the other hand, the presence of probiotics prevents the re-conolization of surfaces by contaminant microorganisms, and is responsible for keeping the hygienic condition of surfaces stable, thus reducing strongly and stably the number and quantity of potentially pathogenic microbial species on the surfaces of hospitals [Vandini et al., 2014—*Hard surface biocontrol in hospitals using microbial-based cleaning products. PLoS One 9, e108598*].

Moreover, the PCHS system has shown to be able to reduce strongly the number of antibiotics resistant bacterial species as well, thus avoiding to select or induce resistant species [Caselli et al., 2016—*Impact of a Probiotic-Based Cleaning Intervention on the Microbiota Ecosystem of the Hospital Surfaces: Focus on the Resistome Remodulation. PLoS One 11, e0148857*].

Since it is a system based on the biologic mechanism of competitive antagonism between probiotic and microbial contaminants, extended treatments are needed, for example at least 30 days of application, to reach a stable reduction of the microbial count.

After such an extended period, the probiotic-based detergents are able to inhibit the occurrence of pathogens on the surface of about 90%, in comparison to the surfaces treated with traditional chemical products [Vandini et al., 2014].

SUMMARY OF THE INVENTION

Aim of the present invention is to solve said problems by providing a product for cleaning, sanitizing and hygienization able to act particularly rapidly and efficiently against any microbial species, of multi-resistant type as well.

Another aim of the invention is to provide a product for cleaning, sanitizing and hygienization with extremely limited environmental impact.

Another aim of the invention is to provide a cleaning and sanitizing product for treatment of surfaces and/or ambients.

The above described aims are obtained by means of a cleaning and sanitizing according to claim 1.

According to particular embodiments the cleaning and sanitizing product object of the invention, comprises one or more of the following features, considered singularly or in combination:

- the concentration of nonionic surfactants is between 0.001-30%, preferably between 5-15%;
- the concentration of cationic surfactants is between 0.001-15%, preferably between 0.001-5%;
- the concentration of amphoteric surfactants is between 0.001-15%, preferably between 0.001-5%;
- the concentration of probiotic bacteria spores is between $10^2$-$10^9$ spores/ml, preferably between $10^6$-$10^7$ spores/ml;
- the concentration of bacteriophage elements is between $10^3$-$10^9$ PFU/ml, preferably between $10^6$-$10^7$ PFU/ml;
- the probiotic bacteria are of the *Bacillus* genus;
- the probiotic bacteria are of the *Bacillus subtilis, Bacillus megaterium* and *Bacillus pumilis* species;
- the bacteriophage elements comprise bacteriophages of the Caudovirales family and/or Microviridae family and/or Leviviridae family and/or Inoviridae family and/or Tectiviridae family and/or Corticoviridae family;

the cleaning and sanitizing product is used for treatment of surfaces and/or ambients.

DESCRIPTION OF THE PREFERRED EMBODIMENTS

The features of the invention will be highlighted in the following as a way of example in the description of some preferred, but not limiting embodiments.

The inventive, proposed cleaning and sanitizing product for cleaning, comprises:
a base solution with sanificant and/or hygienizant action containing at least a surfactant chosen among the nonionic surfactants, cationic surfactants and amphoteric surfactants,
probiotic bacteria spores mixed to such base solution;
bacteriophage elements mixed to such base solution and having bactericidal action on predetermined undesired bacterial species, such bacteriophage elements in cooperation with probiotic bacteria spores being able to carry out a combined and synergistic action against harmful microorganisms.

Nonionic surfactants can occur in the base solution with a concentration between 0.001-30%, preferably between 5-15%.

Cationic surfactants can occur in the base solution with a concentration between 0.001-15%, preferably between 0.001-5%;

Amphoteric surfactants can occur in the base solution with a concentration between 0.001-15%, preferably between 0.001-5%.

The base solution can contain one or more of said nonionic, cationic and amphoteric surfactants in the indicated concentrations.

Probiotic bacteria spores can occur in the base solution with a concentration between $10^2$-$10^9$ spores/ml, preferably between $10^6$-$10^7$ spores/ml.

Bacteriophage elements specifically directed against bacteria persistent on the contaminated surfaces can occur in the base solution with a concentration between $10^3$-$10^9$ PFU/ml, preferably between $10^6$-$10^7$ PFU/ml.

Concerning the probiotic bacteria, as a way of not limiting example, they can be of the *Bacillus* genus, for example they can be the *Bacillus subtilis*, *Bacillus megaterium* and *Bacillus pumilus* species.

It is clear that any other probiotic bacteria can be used according to the undesired bacterial species to be fought.

Advantageously the bacteriophage elements can be chosen, as an alternative or in combination, according to the bacterial species to be fought among the following families: Caudovirales, Microviridae, Leviviridae, Inoviridae, Tectiviridae, Corticoviridae.

As it is known the bacteriophage elements of Caudovirales family comprise also the Myoviridae, Siphoviridae, Podoviridae families.

The proposed cleaning and sanitizing product, in the preferred above described embodiments is particularly indicated for treatment of surfaces and/or ambients, comprising the treatment of inner surfaces of pipes for circulation of fluids for food use (for example water).

The action of bacteriophages is specific, since specific types of lytic bacteriophages kill specific types of bacteria, thus carrying out a potentially very efficient and targeted action in fighting directly against undesired bacteria.

It is also to be highlighted how the use of specific bacteriophages avoids the risk of damage of *Bacillus* probiotics, which thus can keep their activity intact and efficient.

The use of bacteriophages in cleaning and sanitizing products is particularly indicated since they are quite stable in different conditions of temperatures, pH and environmental salinity, and so they can be added to detergents diluted without losing activity.

Lab experimental tests have been carried out which highlight the synergistic effect deriving from the combined use of probiotic bacteria and bacteriophage elements in comparison to the single use of probiotic bacteria or bacteriophage elements.

Test n° 1 (Single Use of Probiotic Bacteria)

The activity of PCHS detergents containing probiotics has been widely evaluated in the field, where it has shown to be able to reduce the microbial count of about 90% more with respect to the traditional detergents, by means of daily use extended for about 1 month.

After a period of 2 months the reduction of contaminant count is stably low both for what concerns bacteria and fungi [Caselli et al., 2016].

Figure 1:
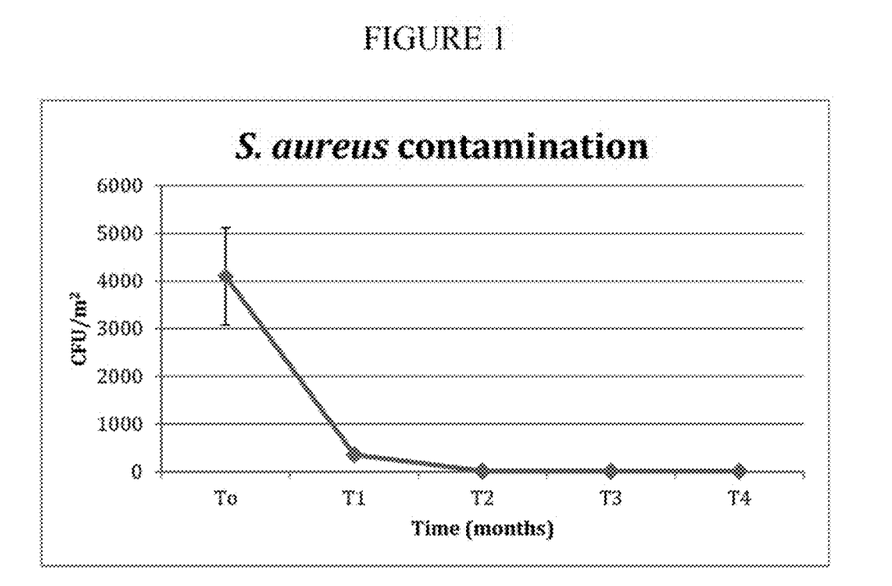
FIGS. 1-3 are graphs relating to colonisation over time, respectively to *Staphylococcus aureus*, Enterobacteriaceae spp. Gram negative) and *Candida albicans*, on surfaces treated with probiotic bacteria.
Figure 2:
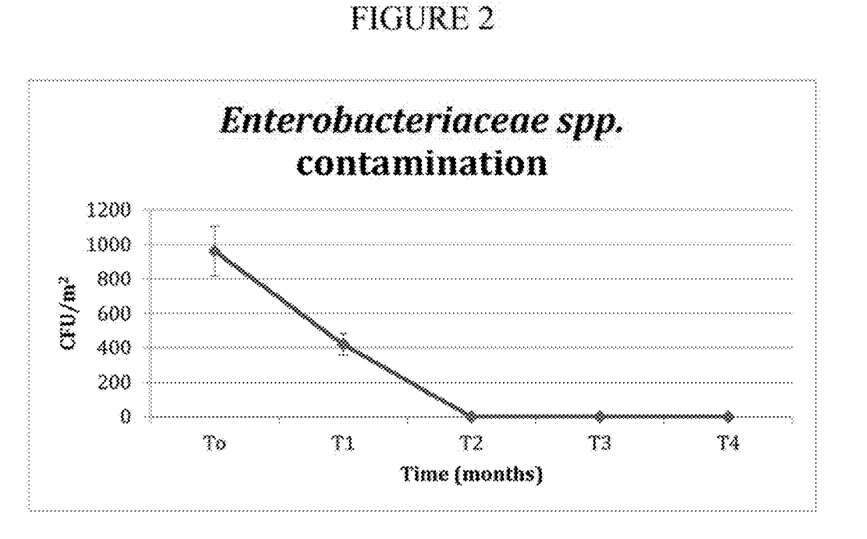
Figure 3:
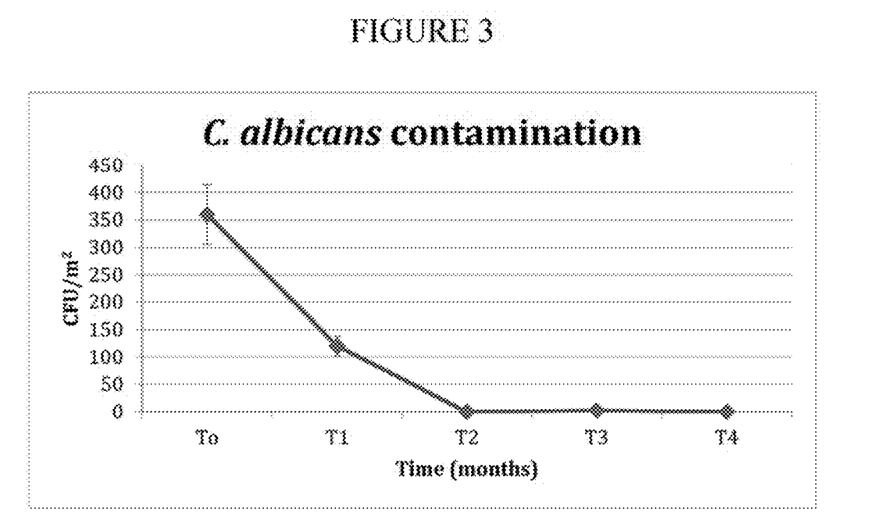

FIGS. 1-2 illustrate the antimicrobial action (bacteria and fungi) of the detergent based only on probiotics.

The development of contamination by *Staphylococcus aureus* (as example of gram-positive bacteria), Enterobacteriaceae spp. (as example of gram-negative bacteria) and *Candida albicans* (as example of fungi) was measured in the field, by application of Rodac plates of culture medium specific for the bacterial and fungi species indicated.

Test n° 2 (Single Use of Bacteriophages)

Figure 4:
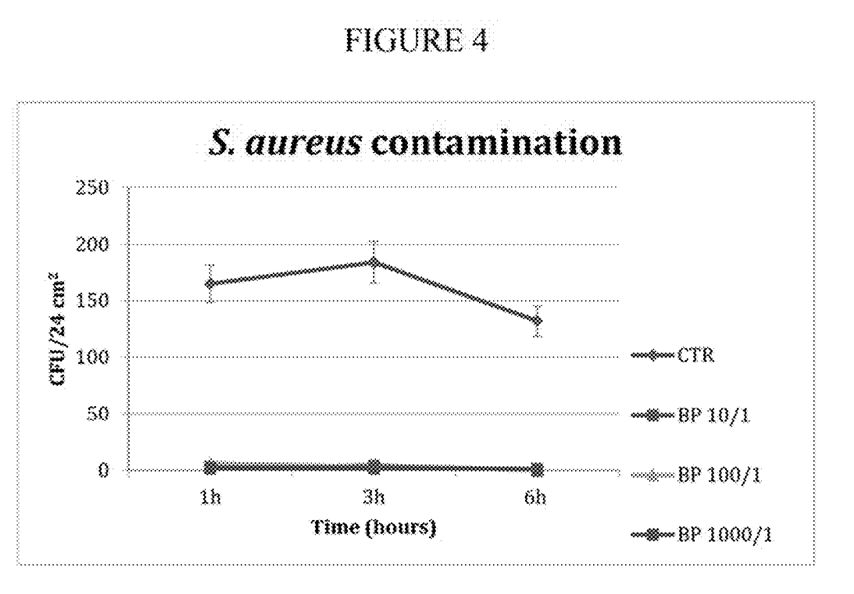
FIGS. 4-6 are graphs relating to colonisation over time, respectively to *Staphylococcus aureus*, Enterobacteriaceae spp. Gram negative) and *Candida albicans*, on surfaces treated with bacteriophages.
Figure 5:
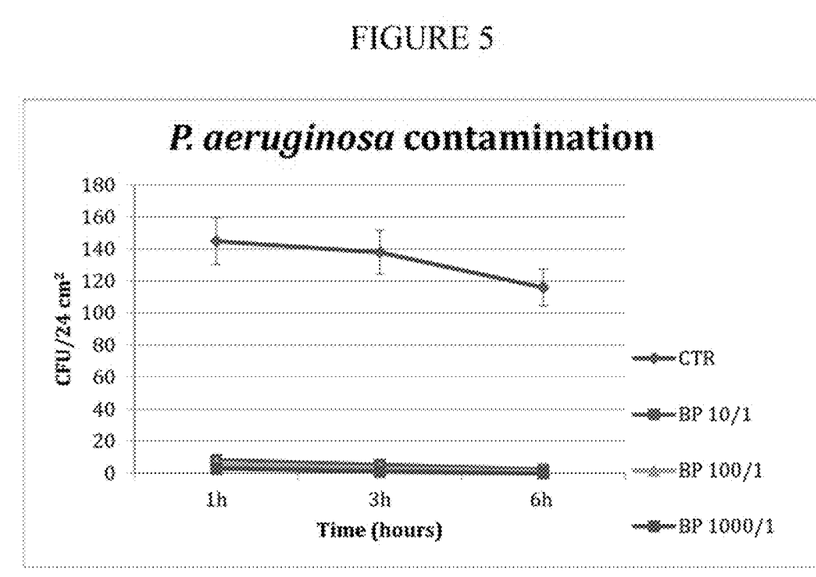
Figure 6:
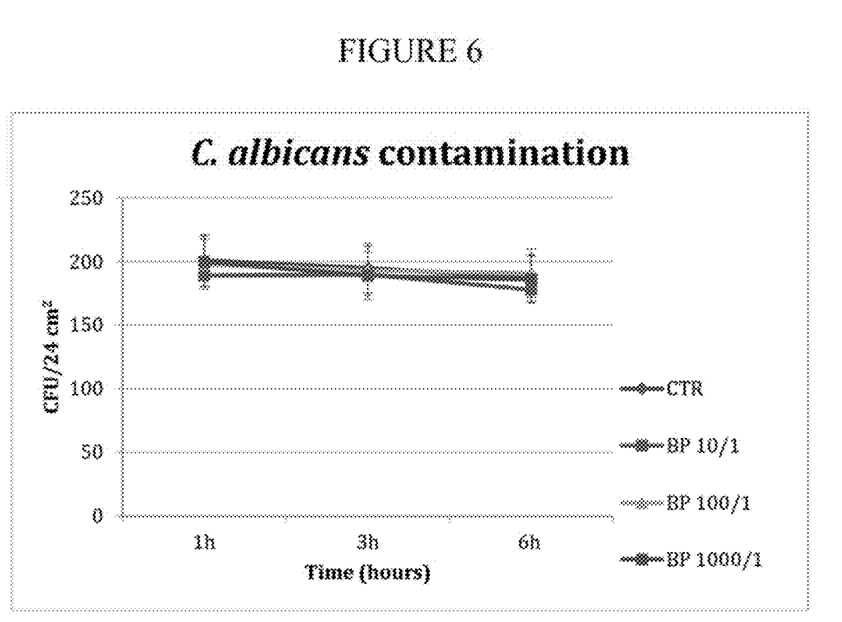

FIG. 4-6 illustrate the antibacterial action of bacteriophages on surfaces contaminated by specific target bacteria.

The development of contamination by *Staphylococcus aureus* (as example of gram-positive bacteria), *Pseudomonas aeruginosa* (as example of gram-negative bacteria) and *Candida albicans* (as example of fungi) was measured in vitro, on experimental models of surfaces of nonporous and sterile material (single fired ceramics 24 cm²).

The surfaces have been contaminated with a known quantity of microorganism ($10^2$ CFU/24 cm²) and in the following treated by application of increasing concentrations of specific bacteriophages ($10^3$, $10^4$, $10^5$ PFU respectively) with ratio 10:1, 100:1 and 1000:1 to the target bacteria in culture.

For fungi it was used the combination of bacteriophages used against gram positive and gram negative bacteria.

The residual contamination was evaluated after 1, 3, 6 hours by application of Rodac plates of culture medium specific for the bacterial and fungi species indicated.

The results are expressed as average values±S.D. of samples in duplicate in three independent experiments.

It can be noted that already after 1 hour, and at the lowest concentration, the bacteriophages are able to eliminate more than 90% of bacterial cells against which they are specifically directed.

The treatments with only bacteriophages has the drawback to be directed against only bacteria specifically recognized by bacteriophages, and so in case of contamination by bacterial species other than the ones against which the bacteriophages are specifically directed, a re-contamination of the treated surface can occur which is due to the fact that the bacteriophages are, by definition, specific for a bacterial species, and so not able to attack other bacterial species, much less to attack fungi species.

These drawbacks of bacteriophages are overcome by adding probiotics, which have instead a slower but generalized action regardless of the bacterial or fungi species occurring.

Test n° 3 (Combined Use of Probiotic Bacteria and Bacteriophages)

Figure 7:
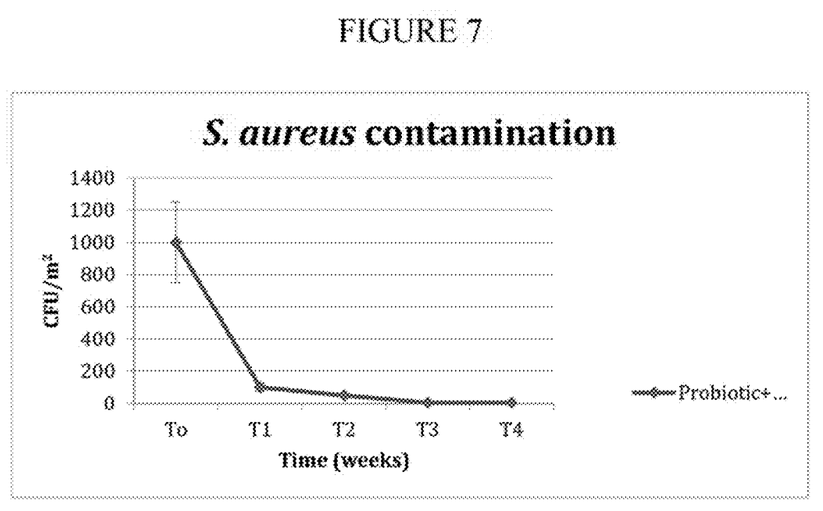
FIGS. 7-9 are graphs relating to colonisation over time, respectively to *Staphylococcus aureus*, Enterobacteriaceae spp. Gram negative) and *Candida albicans*, on surfaces treated with bacteriophages and with probiotic bacteria.
Figure 8:
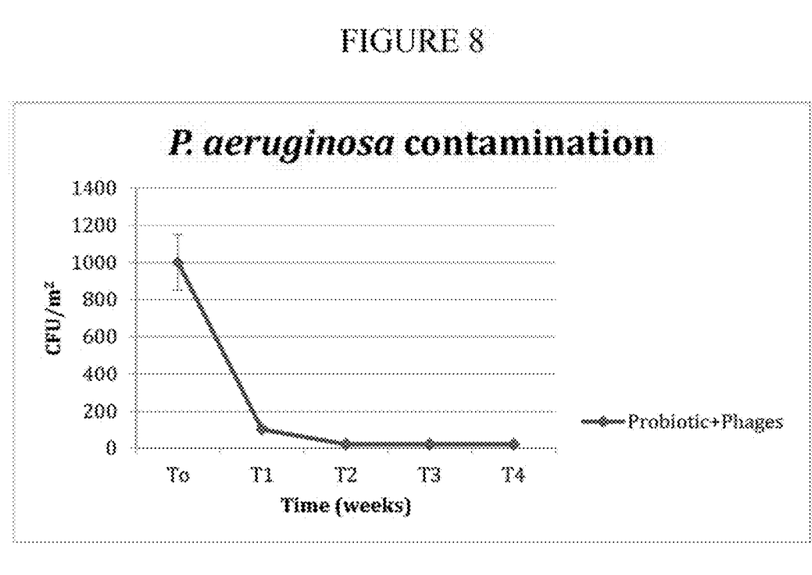
Figure 9:
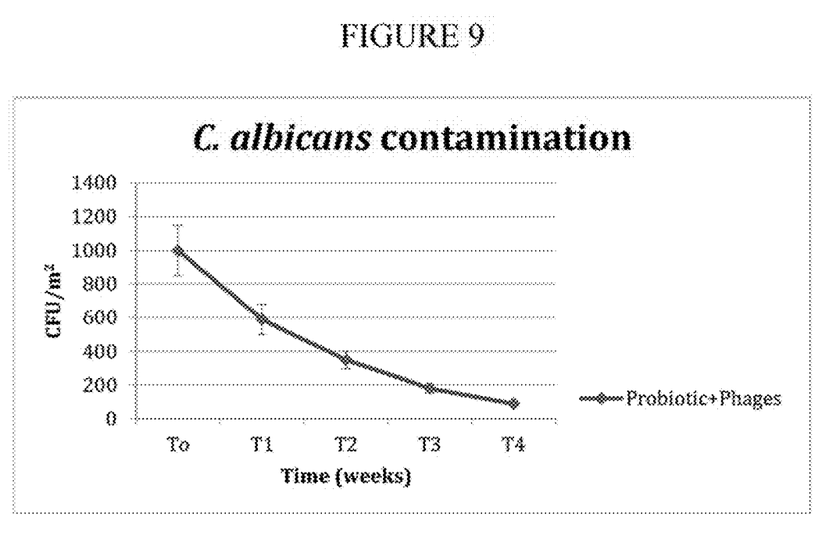

FIGS. 7-9 illustrate the effect of the combined and synergistic antimicrobial action obtained by the contemporaneous occurrence of probiotic bacteria and bacteriophages on surfaces contaminated by the specific microbes shown.

The development of contamination by *Staphylococcus aureus* (as example of gram-positive bacteria), *Pseudomonas aeruginosa* (as example of gram-negative bacteria) and *Candida albicans* (as example of fungi) was measured in vitro, on experimental models of surfaces of nonporous and sterile material (single fired ceramics 24 $cm^2$).

The surfaces have been contaminated with a known quantity of microorganism ($10^3$ CFU/24 $cm^2$) and in the following treated by application of a solution containing probiotic bacteria ($10^3$ PFU/ml) and specific bacteriophages ($10^4$ PFU/ml).

For fungi it was used the combination of bacteriophages used against gram positive and gram negative bacteria.

The residual contamination was evaluated after 1, 2, 3, and 4 weeks by application of Rodac plates of culture medium specific for the bacterial and fungi species indicated. The results are expressed as average values±S.D. of samples in duplicate in three independent experiments.

Comparison of the Tests Carried Out

Figure 10:
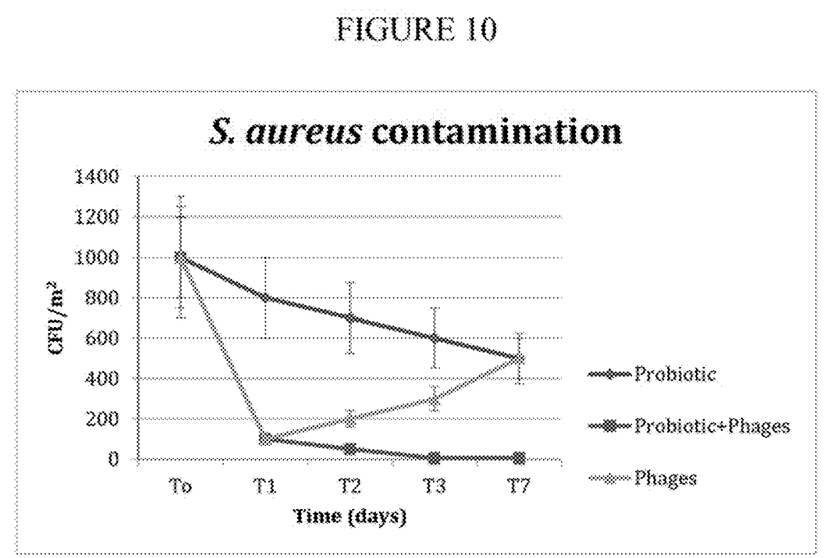
FIG. 10 is a graph relating to colonisation over time, with respect to *Staphylococcus aureus* on surfaces treated with probiotic bacteria and with bacteriophages, with respect to surfaces treated only with probiotic bacteria and only with bacteriophages.

FIG. 10 illustrates the direct comparison of the antimicrobial action of the three treatments on the contamination by *Staphylococcus aureus*, measured in vitro on experimental models of surfaces of nonporous and sterile material (single fired ceramics 24 $cm^2$).

The surfaces have been contaminated with a known quantity of *S. aureus* ($10^3$ CFU/24 $cm^2$) and in the following treated by application of a solution containing only probiotic bacteria ($10^3$ PFU/ml), only specific bacteriophages ($10^4$ PFU/ml), or the combination of probiotics and bacteriophages at the concentrations indicated.

The residual contamination was evaluated after 1, 2, 3, and 7 days by application of Rodac plates of culture medium specific for *Staphylococcus aureus*.

The results are expressed as average values±S.D. of samples in duplicate in three independent experiments.

From the experimental tests carried out, it is to be noted easily how the contemporaneous occurrence of *Bacillus* probiotics and anti-pathogenic bacteriophages increases remarkably the efficacy of the cleaning and sanitizing product, thanks to their synergistic action carried out against the various harmful microorganisms.

On the one hand bacteriophages reduce the contaminant count extremely rapidly but they have a time limited action and are not able to avoid re-contamination.

On the other hand, probiotics reduce the contaminant count slowly by constantly, thanks to the competitive mechanisms, thus inhibiting the re-contamination.

The contemporaneous occurrence of probiotics and bacteriophages guarantees the rapidity of antimicrobial action and at the same time the inhibition of re-contamination, thus guaranteeing a rapid and time stable reduction of pathogens.

The realization of a cleaning and sanitizing product for cleaning which contains at the same time *Bacillus* probiotics and anti-pathogenic bacteriophages is clearly advantageous with respect to the traditional products, in that it guarantees an extremely rapid and immediate reduction of the contaminant bacterial count.

This is due to the combined and synergistic action carried out by the bacteriophage elements which are able to kill the target bacteria in few hours, and by probiotic bacteria which are able to colonize the objects treated persistently, by taking rapidly the place of pathogens.

Therefore the occurrence of bacteriophages represents a strengthening of the antibacterial action of the traditional product based on *Bacillus* probiotics with respect to the pathogens, thus easing and increasing the action of probiotics, which result active on fungi as well.

This guarantees an immediate effect in the initial step of cleaning and sanitizing treatment, thus allowing the probiotic bacteria to determine, in faster times than the traditional products, a low, stable and lasting in time presence of potentially pathogenic bacteria in the ambients and objects treated.

The addition of specific bacteriophage elements to the base solution mixed to probiotic *Bacillus* spores allows advantageously to use the product in targeted way, answering to specific needs and/or situations of particular interest, as for example the reduction of one or more particularly occurring and/or harmful specific bacterial species.

The occurrence of specific bacteriophage elements represents another safety means concerning the use of *Bacillus* probiotics bacteria since above all in the initial steps of attack, those microorganisms are destroyed which are potentially able to give to *Bacillus* undesirable characters by means of gene exchange.

The presence in the inventive product of a greater number of bacteriophage elements families (Caudovirales, Microviridae, Leviviridae, Inoviridae, Tectiviridae and Corticoviridae) allows the same product to have a bactericidal action on a greater group of treatable bacterial species.

The predetermined families of bacteriophage elements can be present in the product object of the invention both singularly and in combination, so that it is contemplated the possibility of diversified treatments according to the specific need.

From what above described it is clear how the proposed cleaning and sanitizing product is able to act against any microbial species, of the multi-resistant type as well ("superbugs"), in a particularly rapid and efficient way with respect to the traditional products indicated in the preamble.

The proposed cleaning and sanitizing product by comprising a base solution with sanificant and/or hygienizing action to which probiotic bacteria and bacteriophage elements are mixed, has decidedly an extremely reduced environmental impact.

Such product is particularly apt for treatment of surfaces and/or ambients comprising the treatment of inner surfaces of pipes for circulation of fluids for food use (for example water).

The invention claimed is:

1. A product for cleaning and sanitizing contaminated surfaces consisting essentially of:
   (a) a base solution with detergent containing at least a surfactant selected from the group consisting of nonionic surfactants, cationic surfactants, amphoteric surfactants and mixtures thereof;
   (b) probiotic bacteria spores mixed to such base solution, wherein the spores are at a concentration of 10 PFU/ml and wherein the bacteria are of the *Bacillus* genus;
   (c) bacteriophage elements mixed to said base solution, where the bacteriophages are at a concentration of $10^4$ PFU/ml and wherein the bacteriophaqe elements are selected from the group consisting of: Caudoverales family, Microviridae family, Leviviridae family, Inoviridae family, Tectiviridae family, Corticoviridae family and mixtures thereof;

wherein the combination of the bacterial spores and the bacteriophage elements have a synergistic action against undesired target pathogens on the contaminated surfaces to thereby provide a rapid onset of antimicrobial action and a time stable inhibition of recontamination.

2. The cleaning and sanitizing product according to claim 1, wherein the probiotic bacteria are selected from the group consisting of the *Bacillus subtilis, Bacillus megaterium* and *Bacillus pumilis* species.

3. The cleaning and sanitizing product according to claim 1, wherein the concentration of nonionic surfactants is between 0.001% and 30%, the concentration of cationic surfactants is between 0.001% and 15%, and the concentration of amphoteric surfactants is between 0.001% and 15%.

4. The cleaning and sanitizing product according to claim 3, wherein the concentration of nonionic surfactants is between 5 and 15%, the concentration of cationic surfactants is between 0.001% and 5%, and the concentration of amphoteric surfactants is between 0.001% and 5%.

* * * * *

UNITED STATES PATENT AND TRADEMARK OFFICE
CERTIFICATE OF CORRECTION

| | | |
|---|---|---|
| PATENT NO. | : 10,683,470 B2 | Page 1 of 1 |
| APPLICATION NO. | : 15/567869 | |
| DATED | : June 16, 2020 | |
| INVENTOR(S) | : Alberto Rodolfi and Elisabetta Caselli | |

It is certified that error appears in the above-identified patent and that said Letters Patent is hereby corrected as shown below:

In the Claims

In Column 7, Line 12, Paragraph (b): currently reads:
(b) probiotic bacteria spores mixed to such base solution, wherein the spores are at a concentration of 10 PFU/ml and wherein the bacteria are of the Bacillus genus;

Should read:
(b) probiotic bacteria spores mixed to such base solution, wherein the spores are at a concentration of $10^3$ PFU/ml and wherein the bacteria are of the Bacillus genus;

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*